United States Patent
Chiu

(10) Patent No.: US 11,479,765 B2
(45) Date of Patent: Oct. 25, 2022

(54) METHOD OF ISOLATING EXOSOMES USING ENCAPSULATION AND AQUEOUS MICELLAR SYSTEM

(71) Applicant: Phase Scientific International, Ltd., Hong Kong (CN)

(72) Inventor: Yin To Chiu, Hong Kong (CN)

(73) Assignee: Phase Scientific International, Ltd., Hong Kong (CN)

( * ) Notice: Subject to any disclaimer, the term of this patent is extended or adjusted under 35 U.S.C. 154(b) by 334 days.

(21) Appl. No.: 16/961,248

(22) PCT Filed: Jan. 18, 2019

(86) PCT No.: PCT/US2019/014312
§ 371 (c)(1),
(2) Date: Jul. 9, 2020

(87) PCT Pub. No.: WO2019/144016
PCT Pub. Date: Jul. 25, 2019

(65) Prior Publication Data
US 2021/0079377 A1    Mar. 18, 2021

Related U.S. Application Data

(60) Provisional application No. 62/619,300, filed on Jan. 19, 2018.

(51) Int. Cl.
*C12N 15/10* (2006.01)
*C07K 1/14* (2006.01)
*G01N 1/40* (2006.01)

(52) U.S. Cl.
CPC .......... *C12N 15/1006* (2013.01); *C07K 1/145* (2013.01); *G01N 1/4044* (2013.01)

(58) Field of Classification Search
CPC ...... G01N 1/4044; G01N 1/6806; G01N 1/34; G01N 33/5005; C07K 1/45
USPC ..................................................... 536/25.4
See application file for complete search history.

(56) References Cited

U.S. PATENT DOCUMENTS

| | | | |
|---|---|---|---|
| 6,132,763 A | 10/2000 | Fisher | |
| 6,399,385 B1 | 6/2002 | Croyle et al. | |
| 7,626,017 B2 | 12/2009 | Laugharn, Jr. et al. | |
| 7,666,583 B2 | 2/2010 | Mor et al. | |
| 7,803,405 B2 | 9/2010 | Keating et al. | |
| 9,823,247 B2 | 11/2017 | Kamei et al. | |
| 10,006,911 B2 | 6/2018 | Kamei et al. | |
| 10,359,423 B2 | 7/2019 | Kamei et al. | |
| 10,578,616 B2 | 3/2020 | Kamei et al. | |
| 2002/0042506 A1 | 4/2002 | Kristyanne et al. | |
| 2005/0077497 A1 | 4/2005 | Anderson | |
| 2006/0025579 A1 | 2/2006 | Riedl et al. | |
| 2006/0166349 A1 | 7/2006 | Kepka et al. | |
| 2007/0161000 A1 | 7/2007 | Van Alstine et al. | |
| 2008/0242825 A1 | 10/2008 | Devi et al. | |
| 2009/0192111 A1 | 7/2009 | Bader et al. | |
| 2009/0286966 A1 | 11/2009 | Christensen et al. | |
| 2010/0174052 A1 | 7/2010 | Hjorth et al. | |
| 2010/0179252 A1 | 7/2010 | Johansson et al. | |
| 2011/0257378 A1 | 10/2011 | Tran et al. | |
| 2011/0263040 A1 | 10/2011 | Jones | |
| 2013/0164825 A1 | 6/2013 | Gabriele et al. | |
| 2014/0221549 A1 | 8/2014 | Bodkhe et al. | |
| 2014/0227712 A1 | 8/2014 | Horlitz | |
| 2014/0228549 A1 | 8/2014 | Bernhard et al. | |
| 2015/0253320 A1 | 9/2015 | Kamei et al. | |
| 2018/0259521 A1 | 9/2018 | Kamei et al. | |
| 2020/0284791 A1 | 9/2020 | Kamei et al. | |

FOREIGN PATENT DOCUMENTS

| | | |
|---|---|---|
| CN | 101679481 A | 3/2010 |
| CN | 110003323 A | 7/2019 |
| EP | 0268946 A2 | 6/1988 |
| WO | 0050161 A1 | 8/2000 |
| WO | 2011159537 A2 | 12/2011 |
| WO | 2015134938 A1 | 9/2015 |
| WO | 2016155888 A1 | 10/2016 |

(Continued)

OTHER PUBLICATIONS

Zhou et al, Langmuir, 2015, 31(48), 13214-13220.*
Shin et al, Scientific Reports 2015, 5, 13103.*
Ziegler YS, et al. (2014) Plasma membrane proteomics of human breast cancer cell lines identifies potential targets for breast cancer diagnosis and treatment. PLoS One. 9(7):e102341.
Schindler J, et al. (2008) Aqueous polymer two-phase systems for the proteomic analysis of plasma membranes from minute brain samples. J Proteome Res 7(1 ):432-442.
Spindler KL, et al. (2015) Circulating free DNA as biomarker and source for mutation detection in metastatic colorectal cancer. PLoS One. 10(4):e0108247.
Riedl W, et al. (2008) Membrane-supported extraction of biomolecules with aqueous two-phase systems[J]. Desalination, 224(1-3): 160-167.

(Continued)

*Primary Examiner* — Ganapathy Krishnan
(74) *Attorney, Agent, or Firm* — Eagle IP Limited

(57) ABSTRACT

The present disclosure relates to a method/system for preparing encapsulated exosomes from a biological sample containing exosomes, said method comprising: a) dispersing inorganic oxide particles into a buffer solution comprising a polymer and a biological sample comprising exosomes, b) allowing the polymer to react with the inorganic oxide particles to form capsules, wherein the exosomes are inside the capsules. The present disclosure also relates to a method/system for isolating and purifying encapsulated exosomes, said method comprising: a) preparing an aqueous micellar system comprising at least one surfactant, and at least one salt; b) mixing a biological sample containing encapsulated exosomes with the aqueous micellar system from step a); c) allowing the aqueous micellar system to phase separate, wherein the surfactant partitions substantially into one phase, and the other phase has a lower concentration of surfactant; and d) obtaining the encapsulated exosomes from the capsule-rich phase.

22 Claims, 1 Drawing Sheet

(56) References Cited

FOREIGN PATENT DOCUMENTS

| WO | 2017041030 A1 | 3/2017 |
|---|---|---|
| WO | 2018039139 A1 | 3/2018 |
| WO | 2018183454 A1 | 10/2018 |
| WO | 2018183465 A1 | 10/2018 |
| WO | 2018222972 A1 | 12/2018 |
| WO | 2019046553 A1 | 3/2019 |
| WO | 2019046563 A1 | 3/2019 |
| WO | 2019055926 A2 | 3/2019 |
| WO | 2019118712 A1 | 6/2019 |
| WO | 2019143895 A1 | 7/2019 |
| WO | 2019143943 A2 | 7/2019 |
| WO | 2019144016 A1 | 7/2019 |
| WO | 2019144030 A1 | 7/2019 |

OTHER PUBLICATIONS

Frerix A, et al. (2005) Scalable recovery of plasmid DNA based on aqueous two-phase separation. Biotechnol Appl Biochem. 42(Pt 1):57-66.
Crucho Cic, et al. (2017) Polymeric nanoparticles: A study on the preparation variables and characterization methods. Mater Sci Eng C Mater Biol Appl. 80:771-784.
Shin H, et al. (2015) High-yield isolation of extracellular vesicles using aqueous two-phase system. Sci Rep. 5:13103.
Zeringer E, et al. (2015) Strategies for isolation of exosomes. Cold Spring Harb Protoc. (4):319-323.
Iqbal M, et al. (2016) Aqueous two-phase system (ATPS): an overview and advances in its applications. Biol Proced Online. 18:18.
Zhou et al. (2015) Nanoparticle Vesicles with Controllable Surface Topographies through Block Copolymer-Mediated Self-Assembly of Silica Nanospheres, Langmuir, vol. 31(48), 11 pages 13214-13220.
Bashir et al. (2016) Controlled-release of Bacillus thurigiensis formulations encapsulated in light-resistant colloidosomal microcapsules for the management of lepidopteran pests of *Brassica* crops, PEERJ., vol. 4(e2524). pp. 1-14.

Sigma-Aldrich "Poly(ethylene glycol) octyl ether" Retrieved from the Internet <URL:https://www.google.com/search?q=poly%28ethylene+glycol%29+octyl+ether&source=lnt&tbs=cdr%3A1%2Ccd_min%3A%2Ccd_max%3A1%2F18%2F2018&tbm=> <URL https://www.sigmaaldrich.com/catalog/product/sigma/40530?lang=en®ion=US> [retrieved on Jun. 16, 2020].

Luechau, Frank; et al. (2009) Primary capture of high molecular weight nucleic acids using aqueous two-phase systems. Separation and purification technology, 66.1: 202-207.

Nazer, Behzad; et al. (2017) Plasmid DNA affinity partitioning using polyethylene glycol-sodium sulfate aqueous two-phase systems. Journal of Chromatography B, 1044: 112-119.

Sorber L, et al. (2017) A Comparison of Cell-Free DNA Isolation Kits: Isolation and Quantification of Cell-Free DNA in Plasma. J Mol Diagn. Jan.;19(1):162-168.

Frank Luechau, et al., Partition of plasmid DNA in polymer-salt aqueous two-phase systems, Separation and Purification Technology, Apr. 20, 2009, pp. 397-404, vol. 66, No. 2, Elsevier Science, Amsterdam, NL.

Vijayaragavan K. Saagar et al., Separation of porcine parvovirus from bovine serum albumin using PEG-salt aqueous two-phase system, Journal of Chromatography B, Sep. 1, 2014, pp. 118-126, vol. 967, NL.

Erik Jue et al., Using an aqueous two-phase polymer-salt system to rapidly concentrate viruses for improving the detection limit of the lateral-flow immunoassay: Concentrating Viruses in a Polymer-Salt System, Biotechnology and Bioengineering, Dec. 1, 2014, pp. 2499-2507, vol. 111, No. 12, US.

Paz Sean et al., A simplified SARS-CoV-2 detection protocol for research laboratories, PLOS One, Dec. 18, 2020, p. e0244271, vol. 15, No. 12.

Steven B. Zimmerman and Lizabeth D. Murphy, Excluded Volume Effects on the Partition of Single- and Double-Stranded Oligodeoxynucleotides Between Two Liquid Phases, Biopolymers, Oct. 1992, 1365-1373, vol. 32, Issue 10, John Wiley & Sons, Inc.

Steven B. Zimmerman and Stefan O. Trach, Excluded Volume Effects on the Partition of Macromolecules Between Two Liquid Phases, Biopolymers, 1990, 703-718, vol. 30, Issue 7-8, John Wiley & Sons, Inc.

T. Matos, et. al., Isolation of PCR DNA fragments using aqueous two-phase systems, Separation and Purification Technology, Feb. 10, 2014, 144-148, vol. 122, Elsevier B.V.

Andreas Frerix, et. al., Exploitation of the Coil-Globule Plasmid DNA Transition Induced by Small Changes in Temperature, pH Salt, and Poly(ethylene glycol) Compositions for Directed Partitioning in Aqueous Two-Phase Systems, Langmuir, Mar. 25, 2006, 4282-4290, vol. 22 Issue 9, American Chemical Society.

* cited by examiner

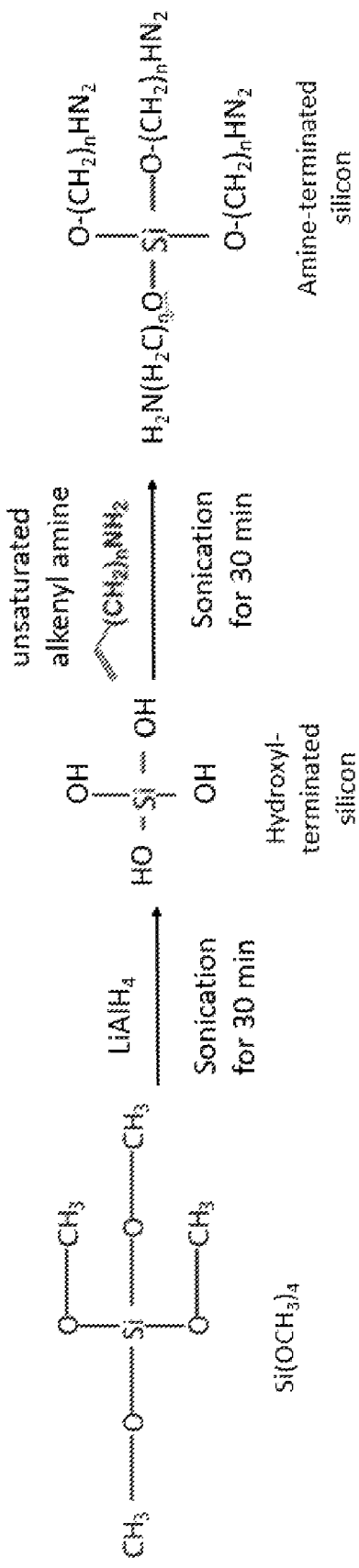

METHOD OF ISOLATING EXOSOMES USING ENCAPSULATION AND AQUEOUS MICELLAR SYSTEM

CROSS-REFERENCE TO RELATED APPLICATIONS

This application claims the benefit of U.S. Provisional Application No. 62/619,300, filed Jan. 19, 2018. The entire contents and disclosures of the preceding application are incorporated by reference into this application.

Throughout this application, various publications are cited. The disclosures of these publications in their entireties are hereby incorporated by reference into this application to more fully describe the state of the art to which this invention pertains.

FIELD OF THE INVENTION

The present invention relates to the isolation and purification of exosomes from biological samples. The exosomes are encapsulated during the isolation and purification so as to preserve the structural and functional integrity of exosomes from any damage. The present invention also provides compositions for the purifications of exosomes. The present invention further relates to the uses and kits for the isolation and purification of exosomes for diagnostic and prognostic methods in a subject.

BACKGROUND OF THE INVENTION

Exosomes are small extracellular vesicles with a size of approximately 30-200 nm in diameter. Exosome is made by a double lipid layer associated with a membrane of proteins. In the past several years, nanoscale vesicles, including exosomes and microvesicles, that originate from cancer cells have been discovered to be circulating in patients' blood. Exosomes are found in abundance in body fluids including blood, saliva, urine, and breast milk (Kosaka et al., Silence 3 (2010) 1-7; Mitchell et al., PNAS 105 (2008) 10513-10518; Palanisamy et al., PLoS One 5 (2010) e8577). The exosomal contents, including nucleic acids and proteins, are found to be representative of the cell of origin. Proteomic and genetic information contained in the exosomes become a useful tool for monitoring and diagnosis of cancer and other diseases.

The most commonly used method for isolating exosomes involves ultracentrifugation steps as disclosed in Thery et al., Curr. Protoc. Cell. Biol., Chapter 3, Unit 3: 22 (2006). The ultracentrifugation steps include the removal of cells and huge debris by centrifugation at 1000 g for 15 minutes, followed by the removal of subcell particles, apoptotic bodies and undesirable organelles by centrifugation at 18,000 g and 4° C. for 30 minutes. After the centrifugation steps, the supernatant needs to be filtered through nylon membranes and to undergo subsequent centrifugation steps to produce pellets of exosomes. However, exosomes have been proven to be difficult to isolate with high purity. The presence of cellular debris and other contaminants may affect the downstream genetic and biochemical analysis of exosomes. This typical approach of concentrating the biological medium using ultracentrifugation before proceeding with exosome isolation is very time-consuming and requires specialized laboratory equipment. Other methods such as affinity chromatography (Taylor & Gercel-Taylor, 2008), size exclusion chromatography (Grant et al, 2011), and chemical-mediated precipitation (Taylor et al, 2011, U.S. Pat. No. 8,901,284) which are known in the art have also been used. However, these existing technologies usually require complicated and time-consuming procedures for isolating extracellular microvesicles and exosomes. In addition, these procedures are limited by the amounts of processing materials.

Despite the evident importance of exosomes, their split and isolation from biological substances while preserving their structural and functional integrity for subsequent studies and uses presents a problem. Conventional methods of isolation and purification of exosomes are difficult to implement, slow and do not guarantee structural and functional conservation of the particles.

Therefore, there remains in the art a need for new methods, compositions, and kits that preserve the structural and functional integrity of exosomes from biological samples during the isolation and purification of exosomes, particularly disease-related and cancer-derived exosomes. The identification of simple and cost-effective methods for handling large volumes of biological materials without the needs for complicated laboratory equipment and ultracentrifugation steps is essential to speeding up the laboratory analysis process. It would be advantageous if the isolation and purification of exosomes can be carried out in an easier and quicker way to speed up the analysis in the laboratory.

The present invention provides that encapsulating the exosomes from biological samples before the isolation and purification can significantly protect the structural and functional integrity of exosomes. Moreover, the present invention provides that the isolation and purification of encapsulated exosomes may be carried out using an aqueous micellar system comprising a composition of at least one surfactant, and at least one salt.

SUMMARY OF THE INVENTION

The present invention provides a method to encapsulate exosomes from biological samples before isolation and purification so as to prevent the exosomes from any damage or lysis.

More particularly, the present invention provides a method to encapsulate the exosomes, wherein the capsules have a wall comprising a hydrophilic polymer and inorganic oxide particles.

In one embodiment, the capsules are formed by the reaction of the hydrophilic polymer with the inorganic oxide particles.

In one embodiment, the hydrophilic polymer is a polymer with a Hydrophile-Lipophile Balance (HLB) value from 0-6, including polyethylene glycol (PEG). In one embodiment, PEG 1000 is preferred.

In one embodiment, the inorganic oxide particles are selected from silicon dioxide, aluminum oxide, titanium dioxide, and any combinations thereof. In one embodiment, silicon dioxide is preferred.

In one embodiment, encapsulated exosomes are prepared by the following procedure:
a) dispersing inorganic oxide particles into a buffer solution comprising a hydrophilic polymer and exosomes;
b) allowing the hydrophilic polymer to react with the inorganic oxide particles to form capsules, wherein the exosomes are enclosed in the capsules; and
c) separating the capsules from the solution via a solid-liquid separation method.

In one embodiment, the solid-liquid separation method for separating the capsules from the solution is selected from filtration, microfiltration, centrifugation, sedimentation or decantation.

In one embodiment, the present invention provides a method for isolating and purifying encapsulated exosomes from biological samples effectively by utilizing an aqueous micellar system. The aqueous micellar system can form at least two phases, wherein one phase has a relatively higher concentration of surfactant (the "surfactant-rich phase") and the other phase has a relatively lower concentration of surfactant (the "surfactant-poor phase"). In one embodiment, the encapsulated exosomes are substantially partitioned in the second phase, i.e., the surfactant-poor phase.

The present invention provides compositions for the purifications of exosomes. The present invention further provides uses of kits for the isolation and purification of exosomes for diagnosis and prognosis of a subject, or for non-diagnostic laboratory uses.

The present invention further provides a method for isolating and purifying encapsulated exosomes from a biological sample, the method comprises the steps of:
a) preparing an aqueous micellar system comprising at least one surfactant, and at least one salt;
b) mixing the biological sample containing encapsulated exosomes with the aqueous micellar system in (a);
c) allowing the aqueous micellar system to phase separate, wherein the surfactant partitions substantially into one phase and the other phase has a lower concentration of surfactant;
d) separating the two phases and collecting the target phase containing encapsulated exosomes; and
e) isolating the encapsulated exosomes from the target phase.

In one embodiment, the aqueous micellar system gives rise to two immiscible phases. Methods such as extraction, filtration, microfiltration, centrifugation, and chromatography can be used to obtain one or both phases from the aqueous micellar system after phase separation.

The present invention provides a method for encapsulating exosomes, which can be carried out before their isolation and purification so that their structural and functional integrity can be preserved. The present invention also provides a method for exosome purification which is highly scalable in terms of time and quantity. It allows different exosomes to be distinguished and purified based on the phase separation of the aqueous micellar system. In one embodiment, the present invention can be adapted for lateral flow chromatography and/or high capacity automation systems.

BRIEF DESCRIPTION OF THE DRAWINGS

FIG. 1 is an example of preparing amine-terminated silicon particles.

DETAILED DESCRIPTION OF THE INVENTION

Herein, unless indicated otherwise, the terms used in the specification including technical and scientific terms have the same meaning as those that are usually understood by those skilled in the art to which the present invention pertains, and detailed description of the known functions and constitutions that may obscure the gist of the present invention will be omitted.

Disclosed herein are methods and compositions for isolating and purifying exosomes using surfactants (such as Triton™) to form an aqueous micellar system. After phase separation of the aqueous micellar system, exosomes can be isolated for further downstream analytical procedures.

Exosomes are one type of spare molecular markers that shed from tumor cells into peripheral circulation. The isolation and purification of exosomes from biological fluids has great potential for routine clinical monitoring of the molecular state of tumors that are difficult to access. Further analysis of the exosomes can provide valuable information on the molecular state of a cancer.

As used herein, the biological sample comprises a body fluid or is derived from a body fluid, wherein the body fluid is obtained from a mammal. In one embodiment, the body fluid is selected from the group consisting of amniotic fluid, aqueous humor, vitreous humor, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and any mixtures thereof.

In some aspects of the invention, the biological sample comprises cultured cells. In some aspects of the invention, the biological sample comprises a sample obtained by liquid biopsy. In some aspects of the invention, the exosomes typically have a diameter of 30-200 nm, more particularly at least 40 nm, or at least 50 nm, or at least 150 nm, or at least 120 nm, or at least 100 nm.

Exosomes are a phospholipid bilayer structure. Exosomes are sensitive to temperature above 38° C. and processing agents, which may damage or lyse the exosome structure. The use of surfactant is carefully controlled when processing and handling the exosome material. According to US20130302822, surfactants, such as Triton™ X-100 and SDS, can lyse exosomes. With the present invention, the exosomes are pre-encapsulated by a hydrophilic polymer so as to prevent the direct contact between exosomes and surfactant during the purification process.

In this invention, a method for encapsulating exosomes is provided and proved to be an effective way to preserve the structural and functional integrity of exosomes.

In one embodiment, the wall of a capsule comprises a hydrophilic polymer and inorganic oxide particles is used for encapsulating the exosomes.

Suitable hydrophilic polymers are polymers with an HLB from 0-6. In one embodiment, the hydrophilic polymer is selected from alkylpolyglycolether polymer, alkylpolyglycoside polymer, polo Amber, and polyethylene glycol (PEG). In one embodiment, the hydrophilic polymer is polyethylene glycol (PEG). In one embodiment, the hydrophilic polymer is PEG having a molecular weight from 1000 to 5000 Da (i.e., PEG 1000-5000). In one embodiment, concentration of the hydrophilic polymers to be used for forming capsules is 1-100 mg/mL. In one embodiment, concentration of the inorganic oxide particles to be used for forming capsules is 0.01-1.25 mol/L.

In this invention, the inorganic oxide particles are preferably particles that have an average particle diameter ($d_{50}$) of less than 1 micron. In one embodiment, the inorganic oxide particles have an average particle size of less than 0.5 µm, or less than 0.25 µm, or less than 0.15 µm. In another embodiment, the inorganic oxide particles have an average particle size of less than 100 nm, or less than 75 nm, or less than 50 nm.

The inorganic oxide particles may be of any suitable inorganic oxide material. In one embodiment, the inorganic oxide material is an oxide of a metal or silicon, or mixtures thereof. In one embodiment, metal oxides are oxides of a metal of Group III, Group IVB or Group VIII of the Periodic Table. In another embodiment, oxides of iron, aluminum, titanium and silicon are used. Accordingly, in one embodiment of this invention, the inorganic oxide particulate material is selected from the group consisting of silicon dioxide, aluminum oxide, mixed oxide of silicon dioxide and aluminum oxide, titanium dioxide, mixed oxide of titanium dioxide and iron oxide, and any combinations thereof.

In one embodiment, the inorganic oxide particles are surface-modified, meaning that the inorganic oxide particle surface has been chemically modified so as to have reactive functional groups capable of forming bonds within the hydrophilic polymer such as PEG. The surface of the particles may be modified using modifying agents selected from a wide variety of chemicals. The reactive functional groups can be epoxy groups, carboxylic groups, unsaturated groups such as acrylic or vinyl groups and amine groups. In one embodiment of the present invention, the surface of the inorganic oxide particles is modified to have amine or amine-terminated groups, in particular alkylamine groups. The amine or amine-terminated groups at the surface of the inorganic oxide particles are able to react with hydroxyl groups on a hydrophilic polymer such as PEG. As a result, a polymer network incorporating the inorganic oxide particles will form. Surface-modified inorganic oxide particles may be prepared by procedures known in the art. For example, J. Mater. Chem., 2009, 19, 5926-5933 teaches a method to synthesize amine-terminated silicon nanoparticles. Methods of surface-modifying silica using silane functional (meth)acrylates are described, e.g., in U.S. Pat. Nos. 4,491,508 and 4,455,205 (Olsen et al.); U.S. Pat. Nos. 4,478,876 and 4,486,504 (Chung); and U.S. Pat. No. 5,258,225 (Katsamberis), which are all incorporated herein by reference.

In one embodiment, functional groups of the inorganic oxide particles react with hydroxyl groups on a hydrophilic polymer to different extent to form capsules. In one embodiment, the extent of reaction is from 3% to 60%. In one embodiment, the extent of reaction is from 3% to 40%. In one embodiment, the extent of reaction is from 3% to 30%.

The capsules may have any suitable particle size. The average particle size of the capsules will generally range from about 1 to about 130 μm, from about 1 to about 100 μm, 1 to about 75 μm, or about 1 to about 50 μm.

The present invention provides a method for encapsulating exosomes. In one embodiment, encapsulated exosomes are prepared by the following procedure:
  a) dispersing inorganic oxide particles into a buffer solution comprising a hydrophilic polymer and exosomes;
  b) allowing the hydrophilic polymer and inorganic oxide particles to react to form capsules; and
  c) separating the capsules from the solution via a solid-liquid separation method.

In one embodiment, encapsulated exosomes are prepared by the following procedure:
  a) dispersing amine-terminated silicon particles into a buffer solution comprising PEG 1000 and exosomes;
  b) allowing PEG 1000 to react with amine-terminated silicon particles to form capsules; and
  c) separating the capsules from the solution via a solid-liquid separation method.

In one embodiment, the solid-liquid separation method for separating the capsules from the solution is selected from filtration, microfiltration, centrifugation, sedimentation or decantation In the present invention, suitable buffers for exosomes include without limitation Tris-EDTA (TE) buffer with compositions comprising tris(hydroxymethyl) aminomethane (Tris), ethylenediamine-tetraacetic acid (EDTA) and polyadenylic acid. In one embodiment, the buffer is 10 mM Tris (pH 8.0), 50 μM EDTA, and 20 μg/mL polyadenylic acid.

After encapsulation of exosomes, the encapsulated exosomes are then isolated and purified from the biological samples by an aqueous micellar system. In one embodiment, the aqueous micellar system can form at least two phases, wherein the surfactant is substantially partitioned into one phase, hence resulting in a first phase which has a relatively higher concentration of surfactant and a second phase has a relatively lower concentration of surfactant.

In one embodiment, the surfactant solution, under selected conditions, is capable of forming a two-phase aqueous micellar system in which one phase is concentrated in surfactant (the "surfactant-rich phase") and the other phase has a low concentration of surfactant (the "surfactant-poor phase"). The conditions under which a two-phase aqueous micellar system may be formed depend on various factors including but not limited to the choice of surfactant molecular structure, temperature, salt conditions, pH, and the presence of polymer (P. Carvalho, et al., Quim. Nova. 31(2):209-213.; Tani, Hirofumi et. al., Anal. Sci. 14. 875-888. 10.2116/analsci.14.875.; Cristina Mazzeu Junqueira et. al., Fluid Phase Equilibria, 478, 14-22). Adjustment of these factors affects the degree of the isolation of exosomes from other contaminating materials in a biological sample. A skilled person in the art will be able to find an effective combination of the parameters of such factors to improve the exosome yield.

In an aqueous solution at concentrations above their critical micelle concentration, the surfactant molecules form micelles. For example, the Triton™ X-114 micellar system exhibits a homogenous and isotropic phase at low temperatures. Upon increasing the temperature, the solution undergoes a macroscopic phase separation to yield a top, micelle-poor phase with low surfactant concentration, and a bottom, micelle-rich phase with high surfactant concentration. Exosomes then distribute, or partition, unevenly between the two phases based on their physicochemical characteristics, such as hydrophobicity and size. By adjusting the concentration of surfactant used, the volume ratio of the two phases can be adjusted and thereby concentrating the exosomes in the top, micelle-poor phase. For example, the initial Triton™ X-114 surfactant concentrations and operating temperatures can be varied in order to achieve the desired volume ratios.

In one embodiment, surfactants in the present invention are non-ionic surfactants. Examples of non-ionic surfactants, which form micelles above their critical micelle concentration, include without limitation commercially available surfactants, such as alkylphenol polyoxyethylene ethers (Triton™ series), polyoxyethylene ethers (Brij® series), polyoxytheylene esters (Myrj™ series), polyoxyethylene sorbitan esters (Tween® series), polyoxyethylene substituted sugar (Glucamate™ series by Amerchol), and other sugar surfactants, such as β-D-alkylglucosides.

In one embodiment, concentration of the surfactant before phase separation is in the range of about 0.001% to about 90% of the total weight of the aqueous solution (w/w). In various embodiments, the surfactant concentration is about 0.005% w/w, about 0.01% w/w, about 0.05% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9%) w/w, about 0.95% w/w, or about 1% w/w. In some embodiments, the surfactant concentration is about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, or about 50% w/w.

In one embodiment, the salt includes but is not limited to kosmotropic salts, chaotropic salts, inorganic salts containing cations such as straight or branched trimethyl ammonium, triethyl ammonium, tripropyl ammonium, tributyl ammonium, tetramethyl ammonium, tetraethyl ammonium, tetrapropyl ammonium and tetrabutyl ammonium, and anions such as phosphates, sulphate, nitrate, chloride and hydrogen carbonate. In another embodiment, the salt is selected from the group consisting of sodium chloride, sodium phosphate, disodium phosphate, potassium phosphate, sodium sulphate, potassium citrate, ammonium sulphate, sodium citrate, sodium acetate and combinations thereof. Other salts, e.g. ammonium acetate, may also be used.

In some embodiments, the total salt concentration before phase separation is in the range of 0.001 mM to 100 mM. A skilled person in the art will understand that the amount of salt needed to form an aqueous two-phase micellar system is influenced by the molecular weight, concentration and physical status of the surfactants.

In various embodiments, the salt solution has a concentration of about 0.001% w/w up to the point of saturation before phase separation. In various embodiments, the salt solution has a concentration of about 0.001% w/w, about 0.05% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9%) w/w, about 0.95% w/w, or about 1% w/w. In some embodiments, the salt solution is selected from surfactant solutions having a salt concentration of about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, and about 50% w/w.

The present invention further provides a method for isolation and purification of encapsulated exosomes from a biological sample, comprising:

a) preparing an aqueous micellar system comprising a composition of at least one surfactant, and at least one salt;
b) mixing the biological sample containing encapsulated exosomes with the aqueous micellar system in (a);
c) allowing the aqueous micellar system to phase separate, wherein said at least one surfactant partitions substantially into one phase; and
d) separating the two phases and collect the target phase containing encapsulated exosomes.
e) separating the encapsulated exosomes from the target phase.

In one embodiment, the aqueous micellar system gives rise to two immiscible phases. Methods such as extraction, filtration, microfiltration, centrifugation, and chromatography can be used to obtain one or both phases from the aqueous micellar system after phase separation.

The present method for encapsulating exosomes can be carried out before isolation and purification so as to preserve the structural and functional integrity of the exosomes.

The present invention also provides a method for exosome purification which is highly scalable in terms of time and quantity. It is capable of distinguishing and purifying different exosomes based on the phase separation of the aqueous two-phase system. In one embodiment, the present invention can be adapted for lateral flow chromatography and/or high capacity automation systems.

In one embodiment, after the purification using the present invention, the purified and concentrated target exosomes can be collected and recovered from the capsules. To recover exosomes from capsules, metal ions are added to destroy the capsules. Metal ions to be used for this purpose can be but is not limited to those of groups 2a (e.g., Mg, Ca), 3a (e.g., Al), 1b (e.g., Cu), 2b (e.g., Zn) and 8b (e.g., Fe, Co, Ni) of the Periodic Table. In one embodiment where PEG is used as the polymer and silicon dioxide is used as the inorganic oxide particles for forming the capsules, since the metal ion has stronger binding affinity for PEG than for silicon dioxide, the exosomes inside the capsules will be released and then collected.

In one embodiment, when the capsules are suspended in TE buffer, metal ion such as magnesium, calcium, iron, cobalt, nickel, aluminum and copper is added to destroy the capsule. As a result, exosomes can be recovered from the TE buffer. In one embodiment, metal ions in TE buffer are selected from Cu(II), Zn(II) or Ni(III).

In one embodiment, the elution buffer for eluting encapsulated exosomes is a TE buffer comprising tris(hydroxymethyl) aminomethane (Tris), ethylenediaminetetraacetic acid (EDTA) and polyadenylic acid. The concentration can be 10 mM Tris (pH 8.0), 50 µM EDTA, and 20 µg/ml polyadenylic acid. The metal ion in the buffer has at least the same molar concentration as the hydrophilic polymer used for capsule preparation.

In one embodiment, by encapsulating the exosomes and isolating the encapsulated exosomes using some embodiments of the present invention, the final yield of exosomes collected by the present invention may be increased up to 35 times more than that of non-encapsulated exosomes (as shown in Table 1 and Table 2). It is expected that exosomes collected by the present invention will have sufficient level of concentration and purity that meets the required standard for an accurate downstream analysis (e.g. diagnosis and prognosis of disease or non-diagnostic laboratory uses).

In conclusion, the present invention represents a significant advancement for the exosome isolation and purification in terms of time and resources. The whole experimental process of the present invention can be automated and carried out in high-throughput operations.

In one embodiment, the present invention provides a method for isolating exosomes from a biological sample, the method comprises:
a. dispersing inorganic oxide particles having reactive functional groups into a buffer solution, said solution comprising a polymer and a biological sample comprising exosomes, wherein the polymer reacts with said reactive functional groups to form capsules encapsulating said exosomes;
b. isolating the capsules, and mixing said capsules with an aqueous micellar system comprising at least one salt and at least one surfactant;
c. allowing phase separation of said aqueous micellar system to give a first phase and a second phase, wherein the first phase has a substantially higher concentration of said surfactant than the second phase, wherein the capsules are concentrated in one of the two phases;
d. isolating the capsules from the capsule-rich phase; and
e. adding a buffer solution of metal ions to the isolated capsules to release the exosomes encapsulated in said isolated capsules.

In one embodiment, the polymer has a Hydrophile-Lipophile Balance (HLB) value of no more than 6.0.

In one embodiment, the reactive functional groups are epoxy groups, carboxylic groups, unsaturated groups, amine groups, amine-terminated groups or alkylamine groups.

In one embodiment, the polymer forms a network with the inorganic oxide particles, thereby encapsulating the exosomes.

In one embodiment, the polymer is polyethylene glycol (PEG). In one embodiment, the polymer is polyethylene glycol (PEG) having a molecular weight ranging from 1000 Da to 5000 Da.

In one embodiment, the inorganic oxide particles have an average particle diameter (d50) of 0.25 to 1 µm. In one embodiment, the inorganic oxide particles have an average particle diameter (d50) of 50 to 100 nm.

In one embodiment, the oxides are metal oxides of Group III, Group IVB or Group VIII of the Periodic Table, or mixtures thereof.

In one embodiment, the polymer reacts to an extent ranging from 3% to 60%. In one embodiment, the polymer reacts to an extent in the range of 3% to 30%.

In one embodiment, the surfactant is a non-ionic surfactant. In one embodiment, the surfactant is alkylphenol polyoxyethylene ethers, polyoxyethylene ethers, polyoxytheylene esters, polyoxyethylene sorbitan esters, polyoxyethylene substituted sugar, or other sugar surfactants and non-ionic surfactants. In one embodiment, the surfactant has a concentration in the range of 0.001% (w/w) to 90% (w/w) of the total weight of said aqueous micellar system.

In one embodiment, the salt is a kosmotropic salt, chaotropic salt or inorganic salt. In one embodiment, the inorganic salt has a cation which can be straight or branched trimethyl ammonium, triethyl ammonium, tripropyl ammonium, tributyl ammonium, tetramethyl ammonium, tetraethyl ammonium, tetrapropyl ammonium or tetrabutyl ammonium. In one embodiment, the inorganic salt has an anion which can be phosphate, sulphate, nitrate, chloride or hydrogen carbonate.

In one embodiment, the salt is sodium chloride, sodium phosphate, disodium phosphate, potassium phosphate, sodium sulphate, potassium citrate, ammonium sulphate, sodium citrate, sodium acetate, ammonium acetate, or combinations thereof.

In one embodiment, the salt in the aqueous micellar system has a concentration of 0.001% up to the point of saturation.

In one embodiment, the metal ions are buffered in a buffer comprising tris(hydroxymethyl)aminomethane (Tris), ethylenediamine-tetraacetic acid (EDTA) or polyadenylic acid.

In one embodiment, the metal ions are selected from the group consisting of Groups 1b, 2a, 2b, 3a and 8b of the Periodic Table. In one embodiment, the metal ions are Cu(II), Zn(II), Mg (II), Ca (II), Ni(III), Fe (II), Fe(III) or Al(III).

This invention will be better understood by reference to the examples which follow. However, one skilled in the art will readily appreciate that the examples provided are merely for illustrative purposes and are not meant to limit the scope of the invention which is defined by the claims following thereafter.

Throughout this application, it is to be noted that the transitional term "comprising", which is synonymous with "including", "containing" or "characterized by", is inclusive or open-ended, and does not exclude additional, un-recited elements or method steps.

EXAMPLES

Example 1—Preparation of Exosomes from Blood

A 1 mL blood sample was centrifuged at no less than 1500 rpm for at least 15 min. Plasma was collected from the supernatant at room temperature. The supernatant was passed through a 70 µm filter and then a 40 µm filter. Exosomes were collected from the filtrate and then dispersed in 50 mL TE buffer containing 10 mM Tris (pH 8.0), 50 µM EDTA and 20 µg/mL polyadenylic acid. The concentration of exosomes was measured by Nanoparticle Tracking Analysis (NTA) to be 800 ng/µL, before being subject to the purification process.

The NanoSight® company commercializes an analysis instrument, the LM10-HS, which allows measuring and characterizing all types of nanoparticles, within a polydisperse sample. Using a 405 nm laser, the nanoparticles are excited and their Brownian motion is monitored by means of an optical microscope and filmed with a camera. The software provided with the apparatus (Nanosight 2.0) allows obtaining an analysis of the size and concentration of the different particles present in the sample.

Example 2—Preparation of Exosomes from Urine

A 1 mL urine sample was centrifuged at no less than 1500 rpm for at least 15 min. Plasma was collected from the supernatant at room temperature. The supernatant was passed through a 70 µm filter and then a 40 µm filter. Exosomes were collected from the filtrate and then dispersed in 50 ml TE buffer containing 10 mM Tris (pH 8.0), 50 µM EDTA, and 20 µg/ml polyadenylic acid. The concentration of exosomes was determined to be 800 ng/µL.

Example 3—General Method to Synthesize Amine-Terminated Silicon Particles

The reaction scheme of this example is illustrated in FIG. 1. 1.5 g of tetraoctylammonium bromide were mixed with 100 mL of dry toluene and the mixture was sonicated for 30 min under a flow of dry argon gas. 100 mL of $Si(OCH_3)_4$ were added via a gas-tight syringe and sonication was continued for 30 min allowing entry of $Si(OCH_3)_4$ into the micelles. Subsequently, 2.3 mL of lithium aluminium hydride (LiAlH$_4$)(1 M in THF) were added in order to form hydroxyl-terminated silicon particles (d$_{50}$=100 nm with narrow size distribution). After a further 30 min sonication, dry and degassed methanol (30 ml) was added to react with the excess LiAlH$_4$. Amine-terminated silicon particles were obtained by the reaction of a degassed amine (2.7 g unsaturated alkenyl amine having 9 carbon atoms) with the hydroxyl-terminated silicon particles under argon, in the presence of 40 mL of 0.05 M chloroplaticnic acid (H$_2$PtCl$_6$) catalyst.

After 30 min sonication, amine-terminated silicon particles were extracted with water, washed with ethyl acetate and filtered twice through syringe membrane filters (Millex, Millipore, PVDF, 0.45 mm).

The resulting amine-terminated silicon particles were further purified by dialysis against water (MWCO 7000, SERVA, Membra-Cel dialysis tubing, diameter 22 mm) to remove any residual, unreacted alkylamine and surfactant.

Example 4—Preparation of Encapsulated Exosomes

The encapsulated exosomes can be prepared by the following procedures:
1. 0.32 g PEG 1000 was dispersed into a 100 mL TE buffer comprising exosomes prepared in Example 1,
2. dispersing 0.09 g of the amine terminated silicon particles prepared in Example 3 into the TE buffer solution from step 1,
3. allowing reaction between PEG 1000 and amine terminated silicon particles to occur to form encapsulated exosomes, and
4. separating the encapsulated exosomes from the solution via filtration.

Example 5—Preparation of Encapsulated Exosomes

The encapsulated exosomes can be prepared by the following procedures:
1. 0.32 g PEG 1000 was dispersed into a 100 ml TE buffer comprising exosomes sample prepared in Example 2,
2. dispersing 0.09 g of the amine terminated silicon particles prepared in Example 3 into the TE buffer solution from step 1,
3. allowing the reaction between PEG 1000 and amine terminated silicon particles to occur in the TE buffer solution to form the encapsulated exosomes, and
4. separating the encapsulated exosomes from the solution via filtration.

Example 6—Isolation and Purification of Encapsulated Exosomes from Aqueous Micellar System The encapsulated exosomes are isolated and purified by the following procedure:
a) providing an aqueous micellar system comprising 3.5 mL of 20 wt % Triton™ X-114, and 3.5 mL of 7.5 wt % potassium phosphate,
b) mixing the encapsulated exosomes isolated in Example 4 with the aqueous micellar system from step (a),
c) allowing phase separation between Triton™ X-114 and potassium phosphate, and
d) separating the two phases and collect the Triton™ X-114 poor phase.
e) obtaining the purified encapsulated exosomes under 1500 rpm centrifugation for 10 min.

The encapsulated exosomes can be further suspended in TE buffer with 0.4 mM Cu(II) solution. The buffer is agitated for 5 min wherein exosomes will be released from the capsules. The quantity of recovered exosomes can be determined by NTA (Nanoparticle Tracking Analysis).

Example 7—Isolation and Purification of Encapsulated Exosomes from Aqueous Micellar System The encapsulated exosomes are isolated and purified by following procedures:
a) providing an aqueous micellar system comprising the composition of 3.5 mL of 20 wt % Triton™ X-114, and 3.5 mL of 7.5 wt % potassium phosphate,
b) mixing the encapsulated exosomes isolated in Example 5 with the aqueous micellar system from step (a),
c) allowing phase separation between Triton™ X-114 and potassium phosphate, and
d) separating the two phases and collect the Triton™ X-114 poor phase.
e) obtaining the purified encapsulated exosomes under 1500 rpm centrifugation for 10 min.

The encapsulated exosomes can be further suspended in TE buffer with 0.4 mM Cu(II) solution. The buffer is agitated for 5 min wherein exosomes will be released from the capsules. The quantity of recovered exosomes can be determined by NTA (Nanoparticle Tracking Analysis).

Example 8—Isolation and Purification of Non-Encapsulated Exosomes from Aqueous Micellar System for Comparison Example 8 follows the procedures in Example 6 using exosomes prepared in Example 1, but the exosomes were not encapsulated.

The amounts of exosomes collected were summarized and compared in Table 1. The results indicate that the quantity of encapsulated exosomes recovered (Example 6) is significantly higher than that of non-encapsulated exosomes (Example 8).

TABLE 1

The quantity and time required of exosomes recovered after purification with an aqueous micellar system

| Example No. | Quantity of collected exosomes (ng) | Yield (compared to example 1) | Time required |
| --- | --- | --- | --- |
| 6 | 700 | 87.5% | 10 min |
| 8 | 20 | 2.5% | 30 min |

Example 9—Isolation and Purification of Non-Encapsulated Exosomes from Aqueous Micellar System for Comparison Examples 9 follows the procedures in Example 7 using exosomes prepared in Example 2, but the exosomes were not encapsulated.

The amounts of exosomes collected were summarized and compared in Table 2. The results indicate that the quantity of encapsulated exosomes recovered (Example 7) is significantly higher than that of non-encapsulated exosomes (Example 9).

TABLE 2

| | The quantity and time required of exosomes recovered after purification with an aqueous micellar system | | |
|---|---|---|---|
| Example No. | Quantity of collected exosomes (ng) | Yield (compared to example 1) | Time required |
| 7 | 710 | 88.7% | 10 min |
| 9 | 20 | 2.5% | 30 min |

What is claimed is:

1. A method for isolating exosomes from a biological sample, comprising the steps of:
   a. dispersing inorganic oxide particles having reactive functional groups into a buffer solution, said solution comprising a polymer and a biological sample comprising exosomes, wherein the polymer reacts with said reactive functional groups to form capsules encapsulating said exosomes;
   b. isolating the capsules, and mixing said capsules with an aqueous micellar system comprising at least one salt and at least one surfactant;
   c. allowing phase separation of said aqueous micellar system to give a first phase and a second phase, wherein the first phase has a substantially higher concentration of said surfactant than the second phase, wherein the capsules are concentrated in one of the two phases;
   d. isolating the capsules from the capsule-rich phase; and
   e. adding a buffer solution of metal ions to the isolated capsules to release the exosomes encapsulated in said isolated capsules.

2. The method of claim 1, wherein said polymer has a Hydrophile-Lipophile Balance (HLB) value of no more than 6.0.

3. The method of claim 1, wherein said reactive functional groups are selected from the group consisting of epoxy groups, carboxylic groups, unsaturated groups, amine groups, amine-terminated groups and alkylamine groups.

4. The method of claim 1, wherein said polymer forms a network with the inorganic oxide particles, thereby encapsulating the exosomes.

5. The method of claim 1, wherein said polymer is polyethylene glycol (PEG).

6. The method of claim 1, wherein said polymer is polyethylene glycol (PEG) having a molecular weight ranging from 1000 Da to 5000 Da.

7. The method of claim 1, wherein said inorganic oxide particles have an average particle diameter (d50) of 0.25 to 1 μm.

8. The method of claim 1, wherein said inorganic oxide particles have an average particle diameter (d50) of 50 to 100 nm.

9. The method of claim 1, wherein said oxide particles are metal oxides, wherein the metal in said metal oxides is selected from Group III, Group IVB and Group VIII of the Periodic Table.

10. The method of claim 1, wherein the polymer reacts to an extent ranging from 3% to 60%.

11. The method of claim 1, wherein the polymer reacts to an extent ranging from 3% to 30%.

12. The method of claim 1, wherein said surfactant is a non-ionic surfactant.

13. The method of claim 1, wherein said surfactant is selected from the group consisting of alkylphenol polyoxyethylene ethers, polyoxyethylene ethers, polyoxytheylene esters, polyoxyethylene sorbitan esters, polyoxyethylene substituted sugars, sugar surfactants and non-ionic surfactants.

14. The method of claim 1, wherein the surfactant has a concentration in the range of 0.001% (w/w) to 90% (w/w) of the total weight of said aqueous micellar system.

15. The method of claim 1, wherein said salt is a kosmotropic salt, chaotropic salt or inorganic salt.

16. The method of claim 15, wherein said inorganic salt has a cation selected from the group consisting of straight or branched trimethyl ammonium, triethyl ammonium, tripropyl ammonium, tributyl ammonium, tetramethyl ammonium, tetraethyl ammonium, tetrapropyl ammonium and tetrabutyl ammonium.

17. The method of claim 16, wherein said inorganic salt has an anion selected from the group consisting of phosphate, sulphate, nitrate, chloride and hydrogen carbonate.

18. The method of claim 1, wherein said salt is selected from the group consisting of sodium chloride, sodium phosphate, disodium phosphate, potassium phosphate, sodium sulphate, potassium citrate, ammonium sulphate, sodium citrate, sodium acetate, ammonium acetate, and combinations thereof.

19. The method of claim 1, wherein the salt in said aqueous micellar system has a concentration of 0.001% up to the point of saturation.

20. The method of claim 1, wherein said metal ions are in a buffer comprising tris(hydroxymethyl)aminomethane (Tris), ethylenediamine-tetraacetic acid (EDTA) or polyadenylic acid.

21. The method of claim 1, wherein the metal of said metal ions is selected from Groups 1B, 2A, 2B, 3A and 8B of the Periodic Table.

22. The method of claim 1, wherein said metal ions are selected from the group consisting of Cu(II), Zn(II), Mg (II), Ca (II), Ni(III), Fe (II), Fe(III) and Al(III).

* * * * *